United States Patent [19]

Heckert et al.

[11] 4,005,117
[45] Jan. 25, 1977

[54] ORGANOSILANE COMPOUNDS

[75] Inventors: David C. Heckert, Oxford; David M. Watt, Jr., Cincinnati, both of Ohio

[73] Assignee: The Procter & Gamble Company, Cincinnati, Ohio

[22] Filed: Apr. 22, 1975

[21] Appl. No.: 570,531

[52] U.S. Cl. .............. 260/448.8 R; 260/448.2 N; 252/548; 428/543
[51] Int. Cl.² ............ C07F 7/10; C07F 7/18
[58] Field of Search ............ 260/448.8 R, 448.2 N

[56] References Cited
UNITED STATES PATENTS

| | | | |
|---|---|---|---|
| 2,972,598 | 2/1961 | Morehouse | 260/448.8 R X |
| 3,389,160 | 6/1968 | Reid | 260/448.2 N |
| 3,471,541 | 10/1969 | Morehouse | 260/448.2 N X |
| 3,557,178 | 1/1971 | Golitz et al. | 260/448.8 R |
| 3,580,920 | 5/1971 | Culpepper | 260/448.8 R X |
| 3,624,120 | 11/1971 | Yetter | 260/448.2 N |
| 3,658,867 | 4/1972 | Prokai | 260/448.2 N |
| 3,661,963 | 5/1972 | Pepe et al. | 260/448.2 N |
| 3,817,739 | 6/1974 | Abbott et al. | 260/448.8 R X |
| 3,836,559 | 9/1974 | Prokai | 260/448.2 N |
| 3,898,257 | 8/1975 | Gregory | 260/448.8 R |

Primary Examiner—Paul F. Shaver
Attorney, Agent, or Firm—C. R. Wilson; R. B. Aylor; T. H. O'Flaherty

[57] ABSTRACT

Organosilanes of formula

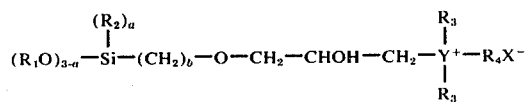

or siloxane oligomers thereof, wherein $R_1$ is an alkyl group containing 1 to 4 carbon atoms or

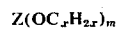

where $x$ is 2 to 4, $m$ is 1 to 20, and Z is hydrogen, an alkyl group containing 1 to 18 carbon atoms or an acyl group containing 1 to 4 carbon atoms; $a$ is 0 to 2; $R_2$ is an alkyl group containing 1 to 18 carbon atoms; $b$ is 1 to 3; $R_3$ is an alkyl, aryl or arylalkyl group containing 1 to 12 carbon atoms, a carboxy-substituted alkyl group containing 1 to 4 carbon atoms,

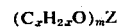

where $x$, $m$ and Z are as defined above, or oxygen provided only one $R_3$ is oxygen; $R_4$ is an alkyl, aryl, or arylalkyl group containing 1 to 22 carbon atoms; X is halide; and Y is nitrogen, phosphorus, or sulfur. The novel compounds are useful for inclusion in a detergent composition for imparting soil release benefits to metallic and vitreous surfaces washed or rinsed therewith.

11 Claims, No Drawings

ORGANOSILANE COMPOUNDS

BACKGROUND OF THE INVENTION

This invention relates to novel organosilane compounds.

Various quaternized substituted organosilane compounds are known. For example, British Pat. No. 686,068 discloses compounds having the general formula $$[(R_3SiCH_2)_aNR^1{}_bH_{4-a-b}]Y$$

where R is an alkyl, monocyclic aryl hydrocarbon or alkoxy radical, $R^1$ is an alkyl, alicyclic hydrocarbon or monocyclic aryl hydrocarbon radical or hydroxy alkyl radical, $a$ is 1 to 2, $b$ is 0 to 3 with $a+b$ being not greater than 4 and Y is an acid anion. These compounds are said to be useful as intermediates in the formation of organosilicon resins, catalysts and emulsifying agents.

U.S. Pat. No. 3,389,160 discloses corrosion inhibitors having the formula $$R_3SiO(SiO)_x(R_2SiO)_ySiR_3$$
$$\text{with substituents } C_2H_4R'CH(OH)CH_2NR_2(R''X)_a \text{ and } R$$

where R is a monovalent hydrocarbon group having up to 18 carbon atoms, R' is a divalent hydrocarbon or hydrocarbonoxy radical having up to 18 carbon atoms, X is an acid anion, R'' is hydrogen or when X is an anion of a halogen acid, R'' is either hydrogen or a group represented by R, $a$ is 0 or 1, $x$ is from 1 to 100, $y$ is from 0 to 1000 and the ratio of $y$ to $x$ is no greater than 50 to 1.

It has now been found that the novel compounds as hereindescribed are useful as an additive to a detergent composition. Commonly assigned copending Patent Application "Organosilane-Containing Detergent Composition" and "Organosilane-Containing Anionic Detergent Composition", both by Heckert and Watt, filed of even date, U.S. Ser. No. 570,534 and 570,533 respectively, disclose detergent compositions containing a class of organosilanes. When metallic or vitreous surfaces are washed with a detergent composition containing the organosilane, a thin polymeric coating of the organosilane is deposited upon the washed or rinsed surfaces. The polymerized coating imparts a soil release benefit to the surface, thereby making the surface easier to clean in subsequent washings.

It is an object of this invention to produce novel organosilane compounds.

It is another object of this invention to produce novel organosilane compounds having utility in a detergent composition.

These and other objects will become apparent from the description to follow.

As used herein all percentages and ratios are by weight unless otherwise indicated.

SUMMARY OF THE INVENTION

Organosilanes of formula $$(R_1O)_{3-a}-\underset{\underset{(R_2)_a}{|}}{Si}-(CH_2)_b-O-CH_2CHOH-CH_2-\underset{\underset{R_3}{|}}{\overset{\overset{R_3}{|}}{Y^+}}-R_4X^-$$

or siloxane oligomers thereof, wherein $R_1$ is an alkyl group containing 1 to 4 carbon atoms or $$Z(OC_xH_{2x})_m$$

where $x$ is 2 to 4, $m$ is 1 to 20, and Z is hydrogen, an alkyl group containing 1 to 18 carbon atoms or an acyl group containing 1 to 4 carbon atoms; $a$ is 0 to 2; $R_2$ is an alkyl group containing 1 to 18 carbon atoms; $b$ is 1 to 3; $R_3$ is an alkyl, aryl or arylalkyl group containing 1 to 12 carbon atoms, a carboxy-substituted alkyl group containing 1 to 4 carbon atoms, $$(C_xH_{2x}O)_mZ$$

where $x$, $m$ and Z are as defined above, or oxygen provided only one $R_3$ is oxygen; $R_4$ is an alkyl, aryl, or arylalkyl group containing 1 to 22 carbon atoms; X is halide; and Y is nitrogen, phosphorus, or sulfur.

DETAILED DESCRIPTION OF THE INVENTION

This invention relates to organosilane compounds having the formula $$(R_1O)_{3-a}-\underset{\underset{(R_2)_a}{|}}{Si}-(CH_2)_b-O-CH_2-CHOH-CH_2-\underset{\underset{R_3}{|}}{\overset{\overset{R_3}{|}}{Y^+}}-R_4X^-$$

or siloxane oligomers thereof wherein $R_1$, $R_2$, $a$, $b$, $R_3$, $R_4$, Y, and X are as defined above. Preferably X is chloride or bromide, $a$ is 0 or 1, $R_3$ is an alkyl group containing 1 to 4 carbon atoms and $R_4$ is an alkyl, aryl or arylalkyl group containing 6 to 12 carbon atoms.

It should be understood that $R_3$ in the above formula may be the same or different. It should further be understood that when Y is sulfur, there will be only one $R_3$ substituent. Also, when one $R_3$ is oxygen or, under basic conditions, the anion of a carboxylic acid substituted alkyl, the counter ion $X^-$ is not extant. The 1 to 4 carbon atoms in the carboxy-substituted alkyl group is inclusive of the carboxyl group.

Classes of organosilanes which fit the above description and having the Formulas I, II, and III and their methods of preparation follow.

$$(R_1O)_{3-a}-\underset{\underset{(R_2)_a}{\diagdown}}{Si}-(CH_2)_b-O-CH_2-CHOH-CH_2-\underset{\underset{R_3}{|}}{\overset{\overset{R_3}{|}}{Y^+}}-R_4X^- \qquad I.$$

wherein $R_1$ is a $C_{1-4}$ alkyl group.

The compounds of Formula I are prepared by initially reacting (when $a$ is 0 and $b$ is 3) trihalosilane with an alcohol ($R_1OH$) at 0° C to 50° C for 1 to 10 hours to produce a trialkoxysilane. This silane is then reacted with an allylglycidylether $$(\underset{\underset{\diagdown\phantom{O}\diagup}{O}}{CH_2=CHCH_2OCH_2CHCH_2})$$

in the presence of 0.01% to 0.1% chloroplatinic acid or platinum at 100° C for 2 to 10 hours. The resultant product $$[(R_1O)_3Si-(CH_2)_3OCH_2\underset{\underset{\diagdown\phantom{O}\diagup}{O}}{CHCH_2}]$$

is reacted with an alkyl substituted tertiary amine, tertiary phosphine, or dialkylsulfide in the presence of an acid in an inert solvent at 60° C to 100° C for 1 to 10 hours to produce the compound of Formula I. Appropriate amines, phosphines or sulfides are used when $R_3$ is aryl or arylalkyl.

The compounds of Formula I when at least one $R_3$ is a carboxy-substituted alkyl group are prepared in the same manner except for the last reaction step. Here, a tertiary amine, tertiary phosphine or dialkylsulfide having a carboxy-containing alkyl group(s) is reacted under a temperature of 200° C for 2 hours to 20 hours. Such carboxy-substituted tertiary amines, tertiary phosphines, and dialkylsulfides are produced by reacting $R_3YHR_4$ or $HYR_4$ (wherein Y is sulfur)

with $X(CH_2)_{1-3}COOH$ in the presence of base at elevated temperatures, e.g., 50° C to 150° C.

The compounds of Formula I when at least one $R_3$ is $(C_xH_{2x}O)_mZ$ with x, m and Z as defined above are produced in the manner given above except for the last reaction step. Thus, there is used a tertiary amine, tertiary phosphine, or dialkylsulfide where at least one substituent is $(C_xH_{2x}O)_mZ$.

The reaction takes place at a temperature of 50° C to 200° C and a time of from 2 to 10 hours.

Compounds of Formula I when one $R_3$ is oxygen are prepared by following the reactions outlined above up to the last reaction step. At this point, a dialkyl amine, dialkyl phosphine or alkylthiol is reacted with the epoxysilane at 50° C to 200° C for from 4 to 10 hours and then with base to produce an intermediate tertiary amine, phosphine, or dialkyl sulfide. These intermediates are then reacted with $H_2O_2$ at 20° C to 100° C or preferably $O_3$ in an inert solvent at −80° C to 20° C to yield the organosilane.

When b is 2 in Formula I, a trihalovinylsilane of formula $X_3SiCH=CH_2$ (which is commercially available) is reacted with hydrogen bromide in the presence of peroxide or light to produce a beta-haloethyltrihalosilane. This compound is reacted with an alcohol, an allylglycidylether, and finally with an appropriate amine, phosphine, or sulfide in the manner discussed above for the preparation of the compounds of Formula I when b is 3.

When b is 1 in Formula I, the starting reactant is a commercially available trihalomethylsilane of formula $X_3SiCH_3$.

This silane is reacted with chlorine or, preferably a half mole of bromine and a half mole of chlorine in the presence of light (such as provided by an ordinary tungsten or fluorescent lamp). The resultant alpha-halomethyltrihalosilane is reacted with an alcohol, an allylglycidylether, and finally an appropriate amine, phosphine or sulfide in the manner discussed above with the compounds of Formula I when b is 3.

When a is 1 or 2, the preparation of the compounds is essentially the same except for the use of an alkyl substituted silane as the starting reactant. The starting reactant is commercially available when $R_2$ is $CH_3$. When $R_2$ is $C_2H_5$ or greater, the compound is prepared by reacting a silane with an appropriate olefin. Thus, $X_{3-a}SiH_{1+a}$ is reacted with a $C_2$ to $C_{18}$ olefin to obtain the desired starting reactant. The remaining reaction steps and conditions for producing the desired organosilane are essentially the same.

The following compounds illustrate the compounds of Formula I.

$(CH_3O)_3Si(CH_2)_3OCH_2CHOHCH_2N^+$ $(CH_3)_2C_{16}H_{33}$ $Cl^-$ $(CH_3O)_2C_{12}H_{25}SiCH_2OCH_2CHOHCH_2N^+$ $(C_3H_6COOH)(C_4H_9)C_8H_{17}$ $Cl^-$ $(C_2H_5O)_3Si(CH_2)_2OCH_2CHOHCH_2N^+$ $(C_2H_4OH)_2C_6H_5$ $Br^-$ $(CH_3O)_3Si(CH_2)_3OCH_2CHOHCH_2N^+$ $(O)^-$ $(CH_3)C_8H_{17}$ $(CH_3O)_3SiCH_2OCH_2CHOHCH_2N^+$ $[(C_2H_4O)H]_2C_{14}H_{29}$ $Br^-$ $(CH_3O)_2C_2H_5SiCH_2OCH_2CHOHCH_2N^+$ $[(C_3H_6O)_{12}C_2H_5](CH_3)_2$ $Cl^-$ $(C_4H_9O)_3SiCH_2OCH_2CHOHCH_2N^+$ $[(C_2H_4O)_3$-$COCH_3]_2CH_3$ $Br^-$ $(CH_3O)_3SiCH_2OCH_2CHOHCH_2P^+$ $(C_4H_9)_2CH_2C_6H_5$ $Br^-$ $(C_4H_9O)_3SiCH_2OCH_2CHOHCH_2P^+$ $(C_2H_4COOH)_2C_8H_{17}$ $Cl^-$ $(CH_3O)_3Si(CH_2)_2OCH_2CHOHCH_2P^+$ $(C_2H_4OH)(C_2H_5)C_{10}H_{21}$ $Cl^-$ $(CH_3O)_3SiCH_2OCH_2CHOHCH_2P^+$ $(O)^-$ $(CH_3)C_{18}H_{37}$ $(CH_3O)_3SiCH_2OCH_2CHOHCH_2P^+$ $[C_3H_6O)_{18}H]_2CH_3$ $Br^-$ $(C_2H_5O)$ $(CH_3)_2SiCH_2OCH_2CHOHCH_2P^+$ $[(C_2H_4O)CH_3]_2C_6H_{13}$ $(CH_3O)_3SiCH_2OCH_2CHOHCH_2S^+$ $(CH_3)C_6H_4CH_3$ $Cl^-$ $(CH_3O)_2C_{16}H_{37}SiCH_2OCH_2CHOHCH_2S^+$ $(C_2H_4COOH)C_8H_{17}$ $Cl^-$ $(CH_3O)_3Si(CH_2)_2OCH_2CHOHCH_2S^+$ $(C_2H_4OH)C_6H_{13}$ $Cl^-$ $(C_2H_5O)_3SiCH_2OCH_2CHOHCH_2S^+$ $(O)^-C_{10}H_{21}$ $(CH_3O)_3SiCH_2OCH_2CHOHCH_2S^+[(C_2H_4O)_{12}H]CH_3$ $Br^-$ $(C_2H_5O)_3SiCH_2OCH_2CHOHCH_2S^+[(C_2H_4O)_2C_8H17]C_2H_5$ $Br^-$

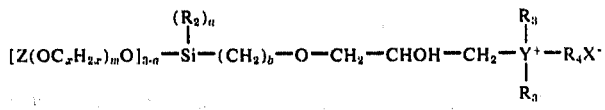

Compounds of Formula II are prepared in a manner identical with that of Formula I except that $R_1OH$ is replaced by

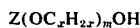

Alternatively, the compounds of Formula I are heated, e.g. at 50° C to 200° C in the presence of

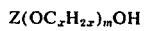

under conditions such that $R_1OH$ is removed from the system.

The following compounds are exemplary of Formula II compounds.

$[H(OC_2H_4)_{20}O]_3SiCH_2OCH_2CHOHCH_2N^+$
  $(CH_3)_2C_{10}H_{21}$ $Cl^-$
$[CH_3(OC_3H_6)_{10}O]_2CH_3SiCH_2OCH_2CHOHCH_2N^+$
  $(C_2H_4COOH)$ $(C_4H_9)_2$ $Cl^-$
$[C_2H_5(OC_2H_4)_2O]_3Si(CH_2)_3OCH_2CHOHCH_2N^+$
  $(C_2H_4OH)_2(C_8H_{17})$ $Cl^-$
$[C_8H_{17}(OC_2H_4)O]_3SiCH_2OCH_2CHOHCH_2N^+$ $(O)^-$
  $(C_4H_9)C_6H_5$
$[CH_3CO(OC_2H_4)_6O]_3Si(CH_2)_2OCH_2$.
  $CHOHCH_2N^+[(C_2H_4O)_{10}H]_2CH_3$ $Cl^-$
$[H(OC_3H_6)_8O]_2C_{16}H_{33}SiCH_2OCH_2CHOHCH_2N^+[(C_2$.
  $H_4O)_8C_4H_9](CH_3)_2$ $Br^-$
$[C_2H_5(OC_2H_4)_4)]_3SiCH_2OCH_2CHOHCH_2N^+[(C_2$.
  $H_4O)_2COCH_3]_2CH_3$ $Br^-$
$[C_{18}H_{39}(OC_2H_4)_3O]_3SiCH_2OCH_2CHOHCH_2P^+$
  $(C_2H_5)_2C_{14}H_{29}$ $Cl^-$
$[H(OC_3H_6)_8]_3Si(CH_2)_3OCH_2CHOHCH_2P^+$
  $(C_3H_6COOH)_2C_6H_{13}$ $Cl^-$
$[C_8H_{17}(OC_2H_4)_2O]_2CH_3SiCH_2OCH_2CHOHCH_2P^+$
  $(C_2H_4OH)$ $(CH_3)C_8H_{17}$ $Cl^-$
$[CH_3(OC_3H_6)O]_3Si(CH_2)_3OCH_2CHOHCH_2P^+$ $(O)^-$
  $(CH_3)C_{10}H_{21}$
$[C_2H_5(OH_4C_2)_{12}O]_3Si(CH_2)_2OCH_2CHOHCH_2P^+[(C_2$.
  $H_4O)_2H]_2C_6H_4CH_3$ $Br^-$
$[CH_3OC(OC_2H_4)_8O]_3SiCH_2OCH_2CHOHCH_2P^+[(C_3$.
  $H_6O)_8C_2H_5](C_4H_9)_2$ $Cl^-$
$[H(OC_2H)_4O]_3SiCH_2OCH_2CHOHCH_2S^+$ $(CH_3)C_{18}H_{37}$
  $Cl^-$
$[C_{16}H_{33}(OC_2H_4)_6O]_2C_{12}H_{21}SiCH_2OCH_2CHOHCH_2S^+$
  $(C_3H_6COOH)C_{10}H_{21}$ $Cl^-$
$[CH_3(OC_4H_8)_4O]_3SiCH_2OCH_2CHOHCH_2S^+$
  $(C_4H_8OH)C_8H_{17}$ $Br^-$
$[H(OC_2H_4)_{14}O]_3Si(CH)_2CHOHCH_2S^+(O)^-C_{12}H_{14}C_6H_5$
$[C_9H_{19}(OC_2H_4)O]_3SiCH_2OCH_2CHOHCH_2S^+[(C_2$.
  $H_4O)_6H]C_6H_{13}$ $Cl^-$
$[C_2H_5OC(OC_2H_4)_2O]_3SiCH_2OCH_2CHOHCH_2S^+[(C_4$.
  $H_8O)_{12}CH_3]C_8H_{17}$ $Cl^-$

These compounds are prepared in a manner similar to that described for the compounds of Example II except that only a part of the $R_1OH$ in the alcoholysis is replaced by

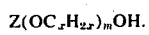

Alternatively, the compounds of Formula I are heated, e.g. at 50° C to 200° C with less than $3-a$ equivalents of

under conditions such that $R_1OH$ is removed from the system.

The following compounds are examples of compounds having the Formula III.

$[H(OC_2H_4)_{12}O](CH_3O)_2SiCH_2OCH_2CHOHCH_2N^+$
  $(CH_3)_2C_{18}H_{37}$ $Cl^-$
$[H(OC_3H_6O)_3O](C_2H_5O)$ $(CH_3)Si(CH_2)_2OCH_2$.
  $CHOHCH_2N^+$ $(CH_2COOH)(C_4H_9)_2$ $Cl^-$
$[C_{12}H_{25}(OC_2H_4)_9O]$ $(C_2H_5O)_2SiCH_2OCH_2$.
  $CHOHCH_2N^+$ $(C_6H_5OH)_2CH_3$ $Cl^-$
$[CH_3(OC_4H_8)_2O]_2(C_4H_9O)Si(CH_2)_3OCH_2$.
  $CHOHCH_2N^+$ $(O)^-(CH_3)$ $C_{16}H_{33}$
$[CH_3CO(OC_2H_4)_6O]_2(CH_3O)SiCH_2OCH_2$.
  $CHOHCH_2N^+[(C_2H_4O)_8H]_2CH_3$ $Br^-$
$[H(OC_2H_4)_{18}O](C_2H_5O)$ $(C_{16}H_{33})SiCH_2OCH_2$.
  $CHOHCH_2N^+[(C_2H_4O)C_{12}H_{25}](CH_3)_2$ $Cl^-$
$[H(OC_2H_4)_8O](C_2H_5O)_2SiCH_2OCH_2CHOHCH_2P^+$
  $(CH_3)_2C_6H_5$ $Cl^-$
$[CH_3(OC_2H_4)_6O](C_{12}H_{25})$ $(CH_3O)SiCH_2OCH_2$.
  $CHOHCH_2P^+[(C_2H_4O)_6OCH_3]_2(CH_3)$ $Cl^-$
$[CH_3CO(OC_3H_6)_4O]_2(CH_3O)Si(CH_2)_3OCH_2$.
  $CHOHCH_2P^+$ $(C_4H_8OH)_2CH_3$ $Cl^-$
$[H(OC_4H_8)_2O](CH_3O)$ $(CH_3)SiCH_2OCH_2$.
  $CHOHCH_2S^+[(C_2H_4O)_3H]C_2H_5$ $Cl^-$
$[C_{12}H_{25}(OC_2H_4O](C_4H_9O)_2Si(CH_2)_2OCH_2$.
  $CHOHCH_2S^+$ $(C_3H_6COOH)CH_3$ $Br^-$
$[C_2H_5CO(OC_2H_4)_{10}O]_2(C_2H_5O)SiCH_2OCH_2$.
  $CHOHCH_2S^+(O)^-C_{12}H_{25}$

Siloxane oligomers of the organosilanes are also useful in the present invention. Such oligomers are formed from the monomers by the controlled addition of from 1 to 100 equivalents of water, preferably in an inert solvent such as alcohol, tetrahydrofuran, etc. As used herein, "oligomers" is used to mean a degree of polymerization of from 2 to 100, preferably from 2 to 20. A higher degree of polymerization adversely affects the ability of the compound to bond itself to the hard surface and is for this reason avoided.

The above organosilanes are useful in a detergent

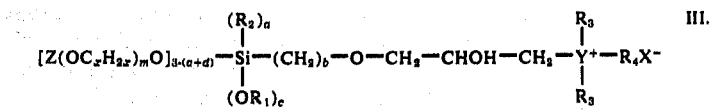

In Formula III, $a$ is 0 or 1, $c$ is 1 or 2 with $(a+c)$ being not greater than 2 and the remaining substituents as defined previously.

composition at a level of organosilane to water-soluble organic detergent of 2:1 to 1:10,000. When metallic or vitreous surfaces are washed or rinsed with a detergent composition containing the organosilane, a soil release benefit is imparted to the surface. It is theorized that the positively charged organosilane is attracted to the negatively charged surface. The silicon atom in the organosilane can then form a bond with the surface. The presence of the positive charge on the organosilane is necessary to allow the bonding to take place under dilute conditions as encountered with detergent composition usage and within a reasonable time period. The terminal alkyl groups attached to the positively charged atom provides the soil release benefits. It is believed that the organosilane compound polymerizes on the surface to form a thin coating of the polymer. The coating is responsible for imparting the soil release benefits to the surface. That is, a hard surface having on it the polymeric coating will be soiled; however, the soil is not tenaciously bound to the surface by virtue of the coating and for this reason is easily washed away.

The examples which follow illustrate the invention.

EXAMPLE I $(CH_3CH_2O)_3Si(CH_2)_3OCH_2CHOHCH_2N^+$
$(CH_3)_2CH_2C_6H_5 \; Cl^-$

One-tenth mole (23.6 gm) of gamma-glycidoxy-propyltrimethoxysilane (commercially available) is placed in a stirred flask equipped with a dry ice condenser. 200 ml of ethanol is added along with an excess of dimethylamine. The mixture is refluxed for 4 hours and allowed to stand over a weekend. Removal of excess dimethylamine and alcohol under reduced pressure leaves a residue having an NMR spectrum as expected for the tertiary amine product wherein the methoxy groups on the silicon have been displaced by ethoxys from the solvent. Fifteen-hundredths of a mole of this product and an equivalent amount of benzyl chloride are dissolved in 30 ml of absolute ethanol and refluxed for one day. NMR analysis indicates complete conversion to the quaternary ammonium salt.

Corresponding organosilanes where a phosphorous atom or a sulfur atom replaces the nitrogen atom are prepared by using a dimethylphosphine or a methylsulfide in place of the dimethylamine in the above reaction step, respectively.

EXAMPLE II $(CH_3CH_2O)_3Si(CH_2)_3OCH_2$-
$CHOHCH_2N^+(CH_3)_2C_{12}H_{25} \; Br^-$

Fifteen-hundredths of a mole of the tertiary amine of Example I is mixed with a like amount of dodecylbromide and 32 ml of absolute ethanol. The mixture is refluxed for one day. NMR analysis indicates complete conversion to the quaternary ammonium salt.

EXAMPLE III $(CH_3O)_3Si(CH_2)_3OCH_2CHOHCH_2N^+(CH_3)\,(C_{12}H_{25})$
$(CH_2CH_2O)_{5.5}H \; Cl^-$

A mixture of 23.6g of

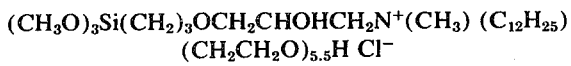

(commercially available) and 47.75gm of the hydrochloride salt of

are heated to 130° C for 18 hours with rapid stirring. The mixture is allowed to cool yielding the indicated ethoxylated quaternary ammoniosilane.

EXAMPLE IV $(CH_3O)_3Si(CH_2)_3CH_2CHOHCH_2N^+(CH_3)$
$[(CH_2CH_2O)_3CH_3]C_{18}H_{37} \; I^-$

A mixture of 23.6 gm of gamma-glycidoxypropyltrimethoxysilane (commercially available) and 28.3 gm of octadecylmethylamine are heated to 130° C for 16 hours with a trace of formic acid.

To this product (26 gm) is added 13.7 gm of $I(CH_2CH_2O)_3CH_3$.

The resulting mixture is heated to 120° C for 8 hours with rapid stirring. NMR analysis indicates that the quaternization is complete.

EXAMPLE V $[H(OC_2H_4)_3O]_3Si(CH_2)_3CH_2$-
$CHOHCH_2N^+(CH_3)_2C_{12}H_{25} \; Br^-$

A rapidly stirred mixture of gamma-glycidoxypropyltrimethoxysilane (23.6g) and carefully dried triethylene glycol (15.0g) is heated to 120° C until 116 ml. (93g) of methanol distills out. The resulting tris-triethylene glycoxy compound is then dissolved in 100 ml. of acetonitrile and 25 g of the hydrochloride salt of dimethyldodecyl amine is added. The resulting mixture is refluxed for 6 hours, cooled, and the solvent is removed leaving the desired quaternary ammonium salt.

What is claimed is:

1. An organosilane of the formula

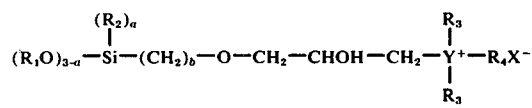

or siloxane oligomers thereof wherein $R_1$ is an alkyl group containing 1 to 4 carbon atoms or $Z(OC_xH_{2x})_m$ where $x$ is 2 to 4, $m$ is 1 to 20, $Z$ is hydrogen, an alkyl group containing 1 to 18 carbon atoms or an acyl group containing 1 to 4 carbon atoms; $a$ is 0 to 2; $R_2$ is an alkyl group containing 1 to 18 carbon atoms; $b$ is 1 to 3; $R_3$ is an alkyl, aryl or arylalkyl group containing 1 to 12 carbon atoms, a carboxy-substituted alkyl group containing 1 to 4 carbon atoms, $(C_xH_{2x}O)_mZ$ where $x$, $m$ and $Z$ are as defined above, or oxygen provided only one $R_3$ is oxygen and further provided that when $R_3$ is oxygen there is no $X^-$; $R_4$ is an alkyl, aryl or arylalkyl group containing 1 to 22 carbon atoms; $X$ is halide; and $Y$ is nitrogen, phosphorus, or sulfur.

2. The organosilane of claim 1 wherein $R_1$ is an alkyl group.

3. The organosilane of claim 1 wherein $R_1$ is $Z(OC_xH_{2x})_m$.

4. The organosilane of claim 1 wherein the siloxane oligomer has a degree of polymerization of from 2 to 100.

5. The organosilane of claim 4 wherein the degree of polymerization is from 2 to 20.

6. The organosilane of claim 1 wherein the organosilane is a monomer.

7. The organosilane of claim 1 wherein X is chloride or bromide.

8. The organosilane of claim 1 wherein $a$ is 0 or 1.

9. The organosilane of claim 1 wherein $R_3$ is an alkyl group containing 1 to 4 carbon atoms.

10. The organosilane of claim 1 wherein $R_4$ contains 6 to 12 carbon atoms.

11. The organosilane of claim 1 having the formula $$(R_1O)_{3-a}\overset{(R_2)_a}{\underset{}{-Si}}-(CH_2)_b-O-CH_2-CHOH-CH_2-\overset{R_3}{\underset{R_3}{-N^+}}-R_4X^-$$

or siloxane oligomers thereof, wherein $R_1$ is an alkyl group containing 1 to 4 carbon atoms or $Z(OC_xH_{2x})_m$ where X is 2 to 4, $m$ is 1 to 20, Z is hydrogen, an alkyl group containing 1 to 18 carbon atoms, or an acyl group containing 1 to 4 carbon atoms; $a$ is 0 to 2; $R_2$ is an alkyl group containing 1 to 18 carbon atoms; $b$ is 1 to 3; $R_3$ is an alkyl, aryl, or arylalkyl group containing 1 to 12 carbon atoms, a carboxy-substituted alkyl group containing 1 to 4 carbon atoms, $(C_xH_{2x}O)_mZ$ wherein $x$, $m$ and Z are as defined above, or oxygen provided only one $R_3$ is oxygen and further provided that when $R_3$ is oxygen there is no $X^-$; $R_4$ is an alkyl, aryl or arylalkyl group containing 1 to 22 carbon atoms; and X is halide.

* * * * *